United States Patent
Ryan et al.

(10) Patent No.: US 10,220,419 B2
(45) Date of Patent: Mar. 5, 2019

(54) INTEGRATED CLEANING AND DISINFECTION DEVICE, SYSTEM AND METHOD

(71) Applicant: RYMED TECHNOLOGIES, LLC, Franklin, TN (US)

(72) Inventors: Dana Wm Ryan, Nolensville, TN (US); James M. Kaiser, Austin, TX (US)

(73) Assignee: RYMED TECHNOLOGIES, LLC, Austin, TX (US)

( * ) Notice: Subject to any disclaimer, the term of this patent is extended or adjusted under 35 U.S.C. 154(b) by 45 days.

(21) Appl. No.: 14/378,850

(22) PCT Filed: Feb. 19, 2013

(86) PCT No.: PCT/US2013/026668
§ 371 (c)(1),
(2) Date: Aug. 14, 2014

(87) PCT Pub. No.: WO2013/123498
PCT Pub. Date: Aug. 22, 2013

(65) Prior Publication Data
US 2016/0015931 A1 Jan. 21, 2016

Related U.S. Application Data

(60) Provisional application No. 61/600,113, filed on Feb. 17, 2012.

(51) Int. Cl.
*B08B 1/00* (2006.01)
*A61M 25/00* (2006.01)
(Continued)

(52) U.S. Cl.
CPC ............... *B08B 1/001* (2013.01); *A61L 2/18* (2013.01); *A61M 25/0097* (2013.01);
(Continued)

(58) Field of Classification Search
CPC ......... B08B 1/001; B08B 1/003; B08B 1/006; A61M 25/0097; A61M 39/16;
(Continued)

(56) References Cited

U.S. PATENT DOCUMENTS

5,713,850 A 2/1998 Heilmann et al.
5,989,227 A 11/1999 Vetter et al.
(Continued)

FOREIGN PATENT DOCUMENTS

WO 2008089196 A2 7/2008

OTHER PUBLICATIONS

International Search Report for International application No. PCT/US13/26668 dated Apr. 2, 2013, 1 page.

*Primary Examiner* — Alexander Markoff
(74) *Attorney, Agent, or Firm* — Hilary Dorr Lang; Patterson Intellectual Property Law, PC

(57) ABSTRACT

A single piece device enables medical clinicians to clean and disinfect both an injection port (needleless I.V. connector) and a vascular access catheter hub. The device has a body with a first end having a blind hole with a wall adapted to be engageable with the threads on the housing of an IV connector and a bottom surface adapted to engage the top surface of the IV connector. The device body has a second end defining a male-luer slip extending out of a recess. The male-luer slip is adapted to extend into a standard vascular access catheter hub such that it engages the inner walls of the catheter hub, and the recess is adapted to receive and be engageable with the outside thread element of the catheter hub.

20 Claims, 2 Drawing Sheets

(51) Int. Cl.
*A61M 39/16* (2006.01)
*A61M 39/18* (2006.01)
*A61L 2/18* (2006.01)

(52) U.S. Cl.
CPC .......... *A61M 39/16* (2013.01); *A61M 39/162* (2013.01); *A61M 39/18* (2013.01); *B08B 1/003* (2013.01); *B08B 1/006* (2013.01); *A61M 2025/0019* (2013.01)

(58) Field of Classification Search
CPC ................ A61M 39/162; A61M 39/18; A61M 2025/0019; A61L 2/18
See application file for complete search history.

(56) References Cited

U.S. PATENT DOCUMENTS

| | | | |
|---|---|---|---|
| 6,045,539 A | 4/2000 | Menyhay | |
| D607,325 S | 1/2010 | Rogers | |
| 7,780,794 B2 * | 8/2010 | Rogers | 134/6 |
| 7,794,675 B2 | 9/2010 | Lynn | |
| 7,922,701 B2 | 4/2011 | Buchman | |
| 7,931,877 B2 | 4/2011 | Steffens et al. | |
| 8,065,773 B2 | 11/2011 | Vaillancourt et al. | |
| 8,167,847 B2 | 5/2012 | Anderson | |
| 8,262,643 B2 | 9/2012 | Tennican | |
| 8,336,151 B2 | 12/2012 | Kerr et al. | |
| 8,336,152 B2 | 12/2012 | Vaillancourt et al. | |
| 8,388,894 B2 | 3/2013 | Colantonio et al. | |
| 8,671,496 B2 | 3/2014 | Vaillancourt et al. | |
| 8,696,820 B2 * | 4/2014 | Vaillancourt | A46B 9/005 134/32 |
| 8,808,637 B2 | 8/2014 | Ferlic | |
| 8,832,894 B2 | 9/2014 | Rogers | |
| 8,999,073 B2 | 4/2015 | Rogers et al. | |
| 2007/0112333 A1 | 5/2007 | Hoang et al. | |
| 2008/0147047 A1 | 6/2008 | Davis et al. | |
| 2008/0177250 A1 | 7/2008 | Howlett et al. | |
| 2009/0008393 A1 | 1/2009 | Howlett et al. | |
| 2009/0028750 A1 | 1/2009 | Ryan | |
| 2009/0241991 A1 | 10/2009 | Vaillancourt et al. | |
| 2010/0172794 A1 | 7/2010 | Ferlic et al. | |
| 2010/0292673 A1 | 11/2010 | Korogi | |
| 2010/0306938 A1 | 12/2010 | Rogers | |
| 2011/0054440 A1 * | 3/2011 | Lewis | A61M 39/16 604/506 |
| 2011/0125104 A1 * | 5/2011 | Lynn | A61M 39/045 604/256 |
| 2011/0232020 A1 | 9/2011 | Rogers | |
| 2011/0265825 A1 | 11/2011 | Rogers | |
| 2012/0016318 A1 * | 1/2012 | Hoang | A61M 39/16 604/288.01 |
| 2012/0039765 A1 * | 2/2012 | Solomon | A61M 25/0097 422/292 |
| 2012/0216359 A1 | 8/2012 | Rogers | |
| 2013/0030414 A1 | 1/2013 | Gardner | |
| 2013/0197485 A1 | 8/2013 | Gardner | |
| 2014/0150832 A1 | 6/2014 | Rogers | |
| 2014/0188089 A1 | 7/2014 | Midgette | |
| 2014/0246616 A1 * | 9/2014 | Fangrow | A61M 39/26 251/148 |
| 2014/0261558 A1 | 9/2014 | Rogers et al. | |
| 2015/0231289 A1 * | 8/2015 | Webb | A61L 2/18 604/192 |

* cited by examiner

INTEGRATED CLEANING AND DISINFECTION DEVICE, SYSTEM AND METHOD

BACKGROUND

1. Field

This specification relates to cleaning and disinfecting devices, systems and methods for medical devices. More particularly, this specification relates to an integrated device that can be used to clean and disinfect both needle-free intravenous connectors (injection ports) and vascular access catheter hubs.

2. State of the Art

Needle-free intravenous ports and connectors were introduced in the late 1980's to reduce the incidence of accidental needlestick injuries that could lead to the transmission of AIDS and Hepatitis to healthcare providers. The intravenous ports and connectors are attached to vascular access catheters to provide the healthcare provider a means to intermittently infuse fluids to the patient and/or aspirate blood from the patient.

Since widespread use of needle-free intravenous connectors began in the early 1990's, a significant increase in intraluminal catheter-related bloodstream infections has occurred. This increase in the number of bloodstream infections has resulted largely from contamination of the IV ports and/or IV connectors by airborne sources and also by direct contamination of the components by the patient or healthcare provider. It has been estimated that this type of catheter-related bloodstream infection has resulted in excess of $25 billion in costs to healthcare facilities worldwide and up to a 25 percent mortality rate.

There is no widely accepted standardized procedure for cleaning and disinfecting intravenous needle-free connectors. Currently, medical practitioners use a 70% isopropyl alcohol pad for swabbing methods that typically involve the application of the disinfectant to the IV connector's surfaces. The current alcohol pads were not designed to clean and disinfect needleless IV connectors or ports. A proper cleaning procedure requires that both the septum and the proximal threaded portion of the needleless intravenous connector are properly cleaned and disinfected to ensure elimination of microorganisms in future uses. However, these swabbing methods are inevitably inconsistent because medical practitioners may inadvertently miss areas or fail to clean threaded areas of the IV connector effectively.

Another source of catheter-related bloodstream infections is the vascular access catheter hub. Needleless IV connectors are routinely changed approximately every 72-96 hours from the vascular access catheter due to infection concerns. When the needleless IV connector is changed and thrown away, the vascular access catheter hubs (1 to 5 hubs per catheter) must be cleaned and disinfected prior to placing new sterile needleless IV connector or connectors. The healthcare provider's hand contamination, particulate matter, blood, patient's skin flora, and other material can contaminate the catheter hub or the threads of the hub, and microorganisms can colonize thereon. Before accessing a catheter hub (e.g., on a central venous catheter line), hand hygiene should be performed, and the catheter hub should be cleaned and disinfected with a 70% isopropyl alcohol or povidone-iodine. Again, while medical practitioners are cautioned to clean the hub, the current cleaning procedures utilized (i.e. 70% isopropyl alcohol pads) are not designed to be used to clean and disinfect vascular access catheter hubs and are often inconsistent because medical practitioners may inadvertently miss areas or fail to clean the threaded area of the hub effectively.

SUMMARY

An integrated cleaning and disinfecting device is provided that enables medical clinicians to effectively clean and disinfect both an injection port (needleless I.V. connector) and a vascular access catheter hub(s) with the single device.

In one aspect, the integrated cleaning and disinfecting device is a single piece of non-particulating absorbent material storing a disinfectant agent in its pores. The material may be plastic. One end of the single piece of absorbent material defines a blind hole having a diameter adapted to be able to engage the threads on the housing of a needleless IV connector. The depth of the blind hole is chosen such that when the blind hole extends over the threaded portion of the IV connector, the top surface of the IV connector (e.g., the septum) can engage the surface on the bottom of the blind hole. In this manner, both the septum and threads of the IV connector may be effectively cleaned and disinfected simultaneously by pushing the first end of the integrated single piece device over the IV connector, optionally squeezing the first end, and rotating back and forth (clockwise and counterclockwise). The second end of the single piece of absorbent plastic defines a male-luer slip extending out of a recess defined in the second end (e.g., an unthreaded male-luer "lock"). The male-luer slip is tapered and is adapted to extend into a standard vascular access catheter hub such that it can engage the inner walls of the standard catheter hub, and the recess is adapted such that it can receive and engage the outside thread element of the catheter hub. In this manner, both the inside and outer thread of the catheter hub may be effectively cleaned and disinfected simultaneously by pushing the second male-luer slip of the absorbent plastic device into the catheter hub opening over the threads of the catheter hub, optionally squeezing the second end, and rotating back and forth (clockwise, and counterclockwise).

In another aspect, the integrated cleaning and disinfecting device with the disinfectant agent is held in a package such as a foil peel type of pouch.

In another aspect, an integrated cleaning and disinfecting device is formed from a single piece of absorbent compressible plastic which stores a disinfectant agent in its pores and is used to effectively clean and disinfect the septum and threads of the female end of a needleless IV connector by engaging a first end of the integrated device with the female end of the needleless IV connector, and is further used to effectively clean and disinfect a vascular access catheter hub by engaging the second end of the integrated device with the female luer-slip and thread element of the catheter hub. In one embodiment, between cleaning and disinfecting the catheter hub and the needleless IV connector, the integrated cleaning and disinfecting device is rotated by one-hundred eighty degrees.

DETAILED DESCRIPTION OF THE PREFERRED EMBODIMENTS

Figure 1A:
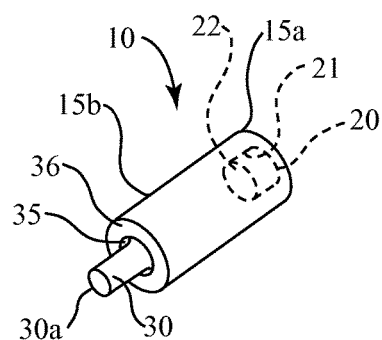
FIGS. 1a and 1b are perspective views of an integrated cleaning/disinfecting device.
Figure 1B:
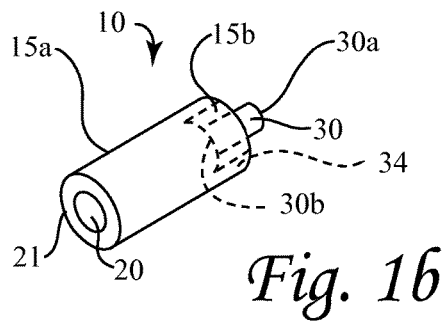
Figure 2:
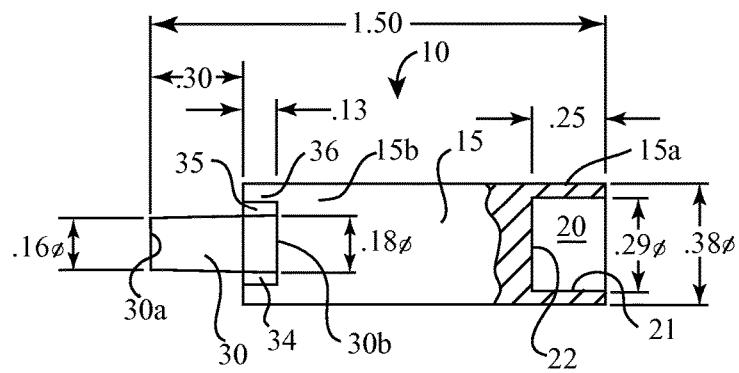
FIG. 2 is a cross-sectional view of the integrated device of FIGS. 1a and 1b.
Figure 3:
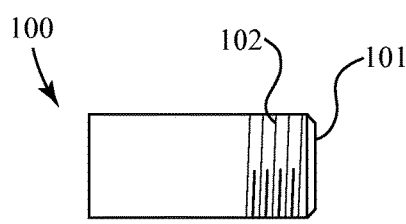
FIG. 3 is a side view of a needleless IV connector.
Figure 4:
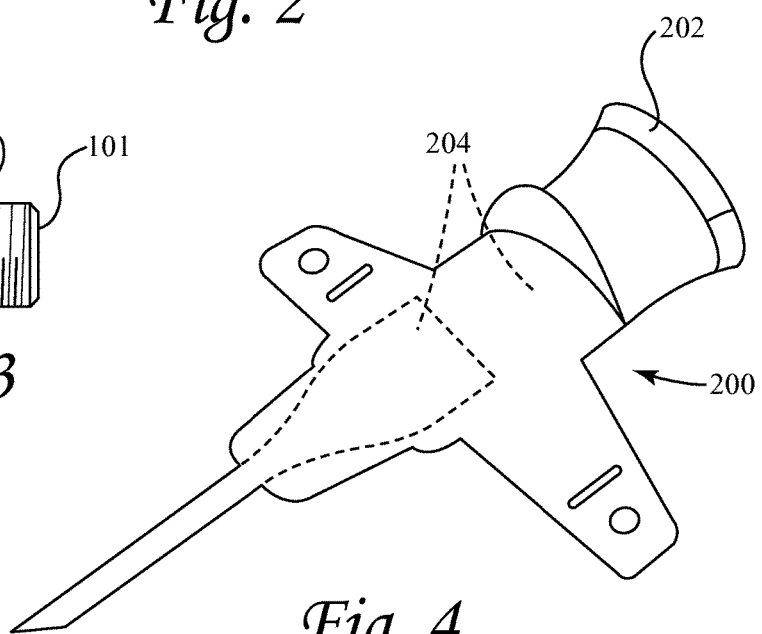
FIG. 4 is a perspective view of a vascular access catheter hub.

An integrated device 10 is seen in FIGS. 1a, 1b, and 2 that enables medical clinicians to effectively clean and disinfect both an injection port (needleless I.V. connector) 100 (FIG. 3) and a vascular access catheter hub 200 (FIG. 4).

The integrated device 10 consists essentially of a single piece of non-particulating absorbent, compressible material which is infused with a disinfectant agent (not shown) in its pores. The disinfectant agent may be 70% isopropyl alcohol, chlorhexidine gluconate (CHG), a combination of the two, povidone-iodine or any other approved disinfectant or disinfectant combination for medical uses. The material may be any suitable material provided it is non-particulating, absorbent and compressible. One such material is plastic (a single plastic or a blend thereof), and for ease of description, the device 10 will be described hereinafter as being a plastic device, although it is not limited thereto.

As seen in FIGS. 1a, 1b, and 2, the single piece of plastic has a body 15 that at one end 15a defines a "blind hole" 20 having a diameter such that the side wall 21 of the blind hole is adapted to engage the threads 102 on the housing of an IV connector (FIG. 3) (i.e., there is either an interference fit, or the first end 15a of device 10 is sufficiently flexible such that it can be squeezed by a practitioner into engagement with the threads). The depth of the blind hole is chosen such that when the blind hole extends over the threaded portion of the IV connector, the top surface of the IV connector (e.g., the septum 104) engages the surface 22 on the bottom of the blind hole 20. In this manner, both the septum 104 and threads 102 of the IV connector 100 may be cleaned and disinfected simultaneously by pushing the first end 15a of the body of the integrated device 10 over the IV connector 100, optionally squeezing the end 15a, and rotating back and forth (clockwise and counterclockwise). The second end 15b of the body of single piece of plastic 10 defines a male-luer slip 30 extending out of a recess 35 defined in the second end (e.g., an unthreaded male-luer "lock"). The male luer-slip extends past a ring 36 (about the recess 35) defined at the end of the body 15b and also extends down into the recess. From tip 30a to base 30b, the male-luer slip is tapered and is adapted to extend into a standard vascular access catheter hub 200 (FIG. 4) such that it engages the inner walls 204 of the standard catheter hub (i.e., there is an interference fit). A recessed wall 34 in the second end 15b of the body 15 defines an annulus around the male-luer slip 30. The annulus is adapted to receive the outside thread element 202 of the catheter hub 200 such that the thread element 202 engages the recessed wall 34 (i.e., there is either an interference fit, or the second end 15b of device 10 is sufficiently flexible such that it can be squeezed by a practitioner into engagement with the outside thread element). In this manner, both the inside 204 and outer thread 202 of the catheter hub may be effectively cleaned and disinfected simultaneously by pushing the male-luer slip 30 of the plastic integrated cleaning/disinfecting device 10 into the catheter hub opening 204 recessed wall 34 extends over the threads 202 of the catheter hub 200, optionally squeezing the end 15b, and rotating back and forth (clockwise and counterclockwise).

For purposes of this specification and the claims, the term "blind hole" shall mean a hole which terminates in a contacting surface, regardless of whether the surface is integral or broken, and regardless of whether the volume beyond the surface is solid or not. Thus, for example, the blind hole may have a bottom surface having a plurality of fingers or extrusions that will clean the top surface (septum) of the IV connector and provide the cleaning/disinfecting when the body is rotated back and forth.

By providing the cleaning/disinfecting device as a single piece of non-particulating, compressible, absorbent plastic, the device can be made extremely inexpensively.

In one embodiment the non-particulating absorbent, compressible plastic is plastic blend comprising EVA. It should be appreciated the plastic should be capable of releasing the disinfecting/cleaning agent from its pores when compressed. Also, for purposes of this specification and the claims, the term "non-particulating" when referring to the plastic body is to be understood as describing a plastic having sufficiently strong molecular bonding so as to prevent particles of plastic from being broken off of the body when the body is subjected to expected frictional forces incurred when the body is rotated over the plastic threads of the catheter hub and the IV connector.

In one embodiment, the non-particulating absorbent, compressible plastic is hydrophilic.

In one embodiment, the non-particulating absorbent, compressible plastic is hydrophobic.

In one embodiment, the non-particulating absorbent, compressible plastic is made into a foam by injection of air or gas during molding.

In one embodiment, the blind hole 20 at the end 15a of the body 15 of the device 10 has a diameter of approximately 0.29 inches. In another embodiment, the blind hole 20 at the end 15a of the body 15 has a diameter of approximately 0.27 inches. In another embodiment, where the material of the body 15 is made of particularly compressible or flexible material, the blind hole 20 at the end 15a of the body 15 has a diameter of approximately 0.45 inches. For purposes of this specification and the claims the terms "approximately" and "about" shall mean plus or minus 10%. In one embodiment, the blind hole 20 at the end 15a of the body has a depth of approximately 0.25 inches. In another embodiment, the blind hole 20 at the end 15a of the body 15 has a depth of approximately 0.27 inches. A depth of about 0.25 inches is preferably a minimum depth, although smaller depths may be used, particularly where the body 15 is made from a very compressible material.

In one embodiment, the luer-slip 30 at the end 15b of the body 15 of the cleaning/disinfecting device 10 has a length of approximately 0.43 inches and extends past the end of the body 15b by approximately 0.30 inches and extends down into recess 35 approximately 0.13 inches. In another embodiment, the luer-slip 30 at the end 15b of the body 15 has a length of approximately 0.47 inches.

In one embodiment the luer-slip 30 tapers from its tip to its base, with the tip being approximately 0.16 inches in diameter and the base being approximately 0.18 inches in diameter.

In one embodiment the recessed wall 34 about the luer-slip base has a diameter of approximately 0.32 inches such that the annulus 35 about the luer-slip base is approximately 0.07 inches wide.

In one embodiment, the integrated cleaning/disinfecting device body 15 is substantially cylindrical and has a diameter of approximately 0.40 inches. In another embodiment, the integrated cleaning/disinfecting device body 15 is substantially cylindrical has a diameter of approximately 0.50 inches. The diameter of the body 15 is chosen such that the wall about the blind hole is substantial enough to withstand the forces applied by the back and forth rotation of the IV connector against the wall without ripping.

In one embodiment, the integrated cleaning/disinfecting device body 15 is cylindrical. In another embodiment the integrated cleaning/disinfecting device body 15 is hyperboloid shaped. In another embodiment, the integrated cleaning/disinfecting body device body 15 is substantially cylindrical with two small indentations along the body which are adapted to receive the fingers of the practitioner.

In one embodiment the length of the integrated cleaning/disinfecting device 10 from the tip 30*a* of the luer-slip 30 to the end of the first end 15*a* of the body 15 is about 1.0 inch. In another embodiment, the length of the integrated cleaning/disinfecting device 10 from the tip 30*a* of the luer-slip 30 to the end of the first end 15*a* of the body 15 is about 1.3 inch. In another embodiment, the length of the integrated cleaning/disinfecting device 10 from the tip 30*a* of the luer-slip 30 to the end of the first end 15*a* of the body 15 is about 1.5 inch. The length of the integrated cleaning/disinfecting device 10 is chosen so that a practitioner can grasp the body 15 of the device 10 between the thumb and forefinger and/or third finger of the practitioner and manipulate the blind hole 20 over a female luer lock of an needleless IV connector until the bottom surface 22 of the blind hole engages the top surface (e.g., septum) of the IV connector, and manipulate the luer slip 30 into the opening of vascular access catheter hub until the walls defining the recess 35 around the luer slip engage the thread of the catheter hub.

Figure 5:
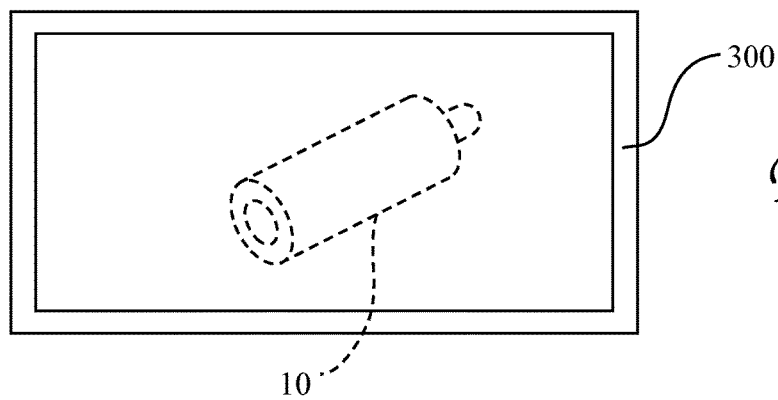
FIG. 5 is a top view of an integrated cleaning/disinfecting device in a peel pouch.

Turning to FIG. 5, the integrated device 10 with the disinfectant agent is held in a package such as a foil peel pouch 300.

Figure 6:
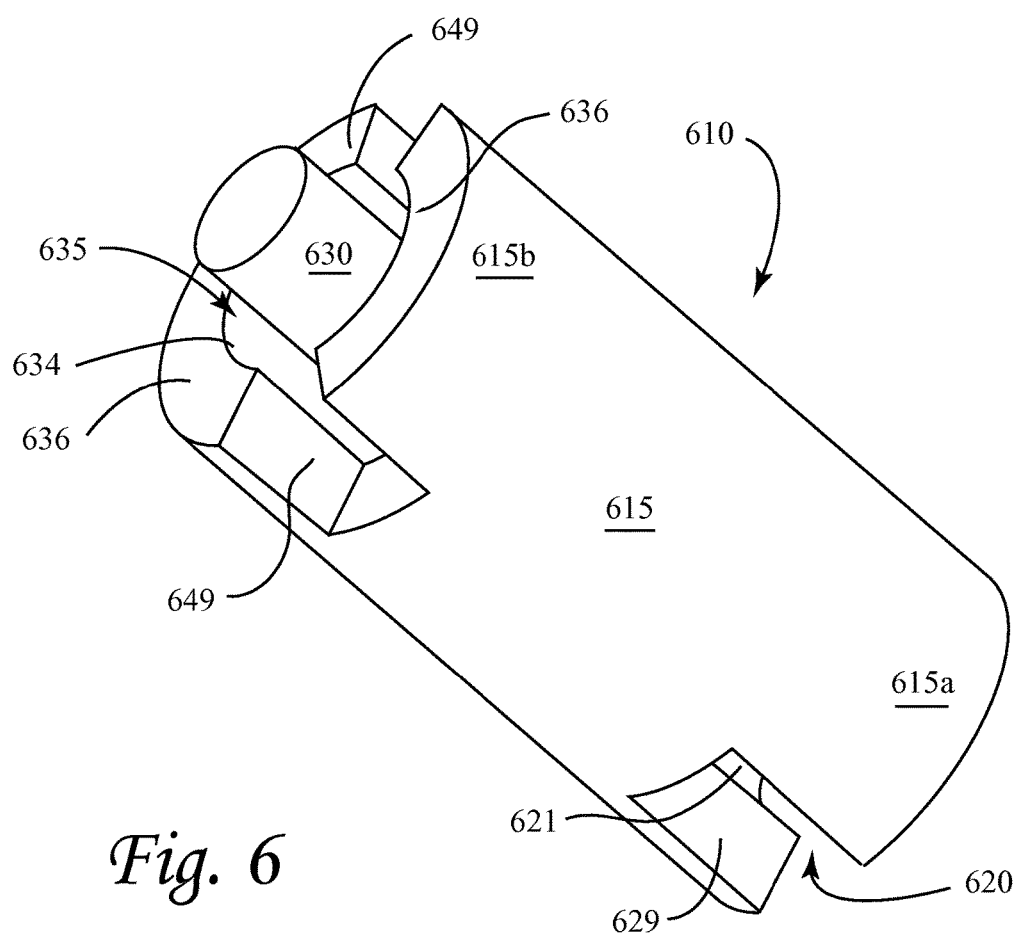
FIG. 6 is a perspective view of another integrated cleaning/disinfecting device.

Another integrated cleaning/disinfecting device 610 is seen in FIG. 6. The integrated cleaning/disinfecting device 610 consists of a single piece of non-particulating, absorbent, plastic which is infused with a disinfectant agent (not shown) in its pores. The single piece of plastic is substantially the same as the single piece of cleaning/disinfecting device 10 of FIGS. 1*a*, 1*b*, and 2, except that the body 615 of device 610 defines slots 629 (only one shown) laterally traversing the outer walls defining the blind hole 620 at one end 615*a* of body 615, and slots 649 laterally traversing the ring 636 around the male luer slip recess 635 at the second end 615*b* of body 615. More particularly, one end 615*a* of body 615 defines a blind hole 620 having a diameter such that the side wall 621 of the blind hole is adapted to engage the threads 102 on the housing of an needleless IV connector (FIG. 3) (i.e., there is an interference fit). The depth of the blind hole 620 is chosen such that when the blind hole extends over the threaded portion of the IV connector, the top surface of the IV connector (e.g., the septum 104) engages the surface on the bottom of the blind hole 620. In this manner, both the septum 104 and threads 102 of the IV connector 100 may be effectively cleaned and disinfected simultaneously by pushing the first end 615*a* of the body of the plastic integrated cleaning/disinfecting device 610 over the IV connector 100 and rotating back and forth (clockwise and counterclockwise). It will be noted that by providing slots 629, it is easier to push the first end 615*a* of the body over the IV connector 100, and engagement of the top surface of the IV connector with the surface of the bottom of the blind hole 620 can be confirmed.

The second end 615*b* of the body of single piece of plastic 610 defines a male luer-slip 630 extending out of a recess 635 defined in the second end (e.g., an unthreaded male-luer "lock"). The male luer slip extends past a ring 636 (about the recess 635) defined at the end of the body 615*b* and also extends down into the recess. From tip to base, the male-luer slip 630 is tapered and is adapted to extend into a standard vascular access catheter hub 200 (FIG. 4) such that it engages the inner walls 204 of the standard catheter hub (i.e., there is an interference fit). A recessed wall 634 in the second end 615*b* of the body 615 defines an annulus around the male-luer slip 630. The annulus is adapted to receive the outside thread element 202 of the needle hub 200 such that the thread element 202 engages the recessed wall 634 (i.e., there is an interference fit). In this manner, both the inside 204 and outer thread 202 of the catheter hub may be effectively cleaned and disinfected simultaneously by pushing the male-luer slip 630 of the integrated cleaning/disinfecting device 610 into the catheter hub opening 204 until the threads 202 of the catheter hub 200 are engaged in the recessed wall 634 of the second end, and rotating back and forth (clockwise and counterclockwise). It is noted that by providing slots 649, it is easier to push the second end 615*b* of the device 610 into the catheter hub.

In one aspect, the integrated cleaning/disinfecting device 610 can have slots in the walls of either end 615*a*, 615*b*, rather than in the walls of both ends.

In another aspect, while two slots are described as provided in the walls of each end 615*a*, 615*b*, either end can have zero, one, two, three, four or more slots.

In another aspect, an integrated cleaning/disinfecting device, e.g., device 10 or 610 formed from a single piece of non-particulating, absorbent, material (e.g., plastic) and storing a disinfectant agent in its pores is used by a practitioner to effectively clean and disinfect the septum and threads of the female end of a needleless IV connector 100 and to effectively clean and disinfect the slip and threads of a catheter hub 200. The practitioner grasps the body 15 (115) of the device 10 (610) with the thumb and forefinger and/or third finger of the practitioner and engages a first end 15*a* (615*a*) of the integrated device with the female end of the needleless IV connector (e.g., by pushing) until the top surface of the IV connector (e.g., the septum 104) engages the surface 22 on the bottom of the blind hole 20 (620). If one or more slots (629) are provided the practitioner can check to see that the top surface of the IV connector is engaging the surface on the bottom of the blind hole. Regardless, the practitioner then rotates the integrated cleaning/disinfecting device 10 (610) relative to and over the IV connector 100 back and forth (rotating clockwise and counterclockwise) a number of times to effectively clean and disinfect the IV connector 100. The practitioner, may, if desired, squeeze the first end 15*a* (615*a*) while rotating the device 10 (610) relative to the IV connector. The practitioner then removes the first end 15*a* (615*a*) from the IV connector 100. The practitioner then rotates the integrated device 10 (610) by one-hundred eighty degrees along the longitudinal axis of the device (i.e., the reverse) in the practitioner's hand. This may be done by putting the device down and picking it up in the reverse orientation, or by rotating the device without putting the device down. The practitioner may then engage the second end 15*b* (615*b*) of the integrated device with the female luer-slip 204 as the second end extends over the thread element 202 of the vascular access catheter hub 200 (e.g., by pushing). The practitioner then rotates the device 10 (610) relative to and over the catheter hub 200 back and forth (clockwise and counterclockwise) a number of times to effectively clean and disinfect the catheter hub 200. The practitioner, may, if desired, squeeze the second end 15*b* (615*b*) while rotating the device 10 (610) relative to the catheter hub 200. The practitioner then removes the second end 15*b* (615*b*) from the IV connector.

It will be appreciated that the order of disinfection of the IV connector 100 and the catheter hub 200 can be switched. It will also be appreciated that squeezing is optional if the first and second ends are adapted to be in an interference fit with the IV connector threads and the catheter hub thread. On the other hand, if one or the other or both ends are not adapted to be in an interference fit, squeezing may be necessary to cause the end or ends of the integrated device to engage the IV connector and/or the catheter hub.

Where a foil (peel-type) pouch 300 is provided, prior to grasping the body 15 (615) of the device 10 (610), the practitioner opens or has an assistant open the pouch.

There have been described and illustrated herein several embodiments of an integrated cleaning/disinfecting device and method of using the integrated cleaning/disinfecting device. While particular embodiments have been described, it is not intended that the invention be limited thereto, as it is intended that the invention be as broad in scope as the art will allow and that the specification be read likewise. Thus, while a particular non-particulating, absorbent plastic material has been disclosed, it will be appreciated that other non-particulating, absorbent materials such as cotton, foams, natural materials, other plastics or plastic blends, or their equivalents could be used as well. What is particularly important is that the material be compressible, capable of storing a disinfectant agent, releasing the disinfectant agent when compressed, and remain intact even after being subjected to repeated frictional engagement (i.e., it will not release particles). In addition, while particular types of disinfectant agent have been disclosed, it will be understood that other types of disinfectant agents can be used. Also, while particular dimensions for the blind hole has been disclosed, it will be recognized that other similar dimensions can be utilized provided the walls of the blind hole can be engaged with the threaded portion of the IV connector (e.g., through a friction fit or by squeezing the walls), and when the wall of the blind hole engages the threads of the IV connector, the top surface of the needleless IV connector engages the surface on the bottom of the blind hole. Similarly, while particular dimensions for the luer-slip, and the annulus about the luer-slip have been disclosed, it will be recognized that other similar dimensions can be utilized provided there is an interference between the luer-slip and the inside wall of the vascular access catheter hub(s) and the wall about the annulus of the cleaning/disinfecting device can engage the thread of the catheter hub (e.g., through a friction fit or by squeezing the wall). Also, while the cleaning/disinfecting device has been described as consisting of a single piece of non-particulating, absorbent plastic or an equivalent thereof in conjunction with the disinfectant agent, it will be appreciated that other elements which do not substantially add to the functionality of the device could be provided, such as a wrapping about the central portion of the body, a gauze or pad on the inside of the blind hole, or other similar elements. Thus, the integrated cleaning/disinfecting device can consist essentially of the single piece of non-particulating, absorbent plastic or the equivalent thereof in conjunction with the disinfectant agent. It will therefore be appreciated by those skilled in the art that yet other modifications could be made without deviating from its spirit and scope of the claims.

What is claimed is:

1. A device for use in cleaning and disinfecting an intravenous (IV) connector having a female luer having an external thread and a top surface, and for use in cleaning and disinfecting a vascular access catheter hub having an internal wall and an external thread, said device consisting essentially of:
   a single piece of non-particulating compressible material having pores infused with a disinfectant agent,
   said single piece of material having a body with a first end and a second end,
   said first end defining a blind hole having a side wall and a bottom surface, said side wall adapted to be engageable with the external thread of the IV connector, and said blind hole having a depth chosen such that when said blind hole extends completely over the external thread of the IV connector, the top surface of the IV connector engages said bottom surface of the blind hole,
   said second end defining an annular recess with a ring having an inner wall about the annular recess at the second end of said body, and a male-luer slip extending from inside said recess to outside of said recess, said male-luer slip having a base inside said recess and a tip beyond said ring, said male-luer slip adapted to extend into the vascular access catheter hub and engage the internal wall of the catheter hub with an interference fit, and said inner wall of said ring adapted to be engageable the external thread of the catheter hub when the male-luer slip engages the internal wall of the catheter hub.

2. A device according to claim 1, wherein:
said non-particulating compressible material comprises plastic.

3. A device according to claim 1, wherein:
said blind hole has a depth of at least 0.25 inches.

4. A device according to claim 1, wherein:
said luer-slip has a length of at least 0.43 inches from said base to said tip.

5. A device according to claim 1, wherein:
said tip of said luer-slip has a diameter of approximately 0.16 inches and said base of said luer-slip has a diameter of approximately 0.18 inches, and said luer-slip tapers from said base to said tip.

6. A device according to claim 5, wherein:
said inner wall is spaced approximately 0.07 inches from said luer-slip base.

7. A device according to claim 3, wherein:
said luer-slip has a length of at least 0.43 inches from said base to said tip, and said tip of said luer-slip has a diameter of approximately 0.16 inches, and said base of said luer-slip has a diameter of approximately 0.18 inches, and said luer-slip tapers from said base to said tip.

8. A device according to claim 7, wherein:
said body is substantially cylindrical and has a diameter of at least 0.40 inches and a length of at least 1.0 inch including said luer-slip.

9. A device according to claim 1, wherein:
said body is substantially cylindrical and has a diameter of at least 0.40 inches and a length of at least 1.0 inch including said luer-slip.

10. A device according to claim 1, wherein:
said non-particulating material is hydrophilic.

11. A device according to claim 1, wherein:
at least one of said first end side wall and said ring defines at least one lateral slot.

12. A device according to claim 11, wherein:
both said first end side wall and said ring define at least one lateral slot.

13. A device according to claim 1 in conjunction with a foil package thereabout.

14. A method of cleaning and disinfecting an intravenous (IV) connector having a female luer having an external thread and a top surface, and a vascular access catheter hub having an internal wall and an external thread, said method comprising:
   a) obtaining a device consisting essentially of a single piece of non-particulating compressible material having pores infused with a disinfectant agent, said single piece of material having a body with a first end and a second end, said first end defining a blind hole having a side wall and a bottom surface, said side wall adapted to be engageable with the external thread of the IV connector, and said blind hole having a depth chosen such that when said blind hole extends completely over the external thread of the IV connector, the top surface of the IV connector engages said bottom surface of the blind hole, said second end defining an annular recess with a ring having an inner wall about the annular recess at the second end of said body, and a male luer-slip extending from inside said recess to outside of said recess, said male-luer slip having a base inside said recess and a tip beyond said ring, said male-luer slip adapted to extend into the vascular access catheter hub and engage the internal wall of the catheter hub with an interference fit, and said inner wall of said ring adapted to be engageable the external thread of the catheter hub when the male-luer slip engages the internal wall of the catheter hub;
   b) grasping said device in a first orientation and pushing said device relative to said IV connector such that said blind hole extends over said female luer of said IV connector and so that said side wall of said first end of said device engages said external thread of said IV connector and said bottom surface of said blind hole engages said top surface of said IV connector;
   c) with said side wall engaging said external threads and said bottom surface engaging said top surface, rotating said device relative to said IV connector a plurality of times;
   d) removing said device from over said female luer of said IV connector;
   e) grasping said device in a second orientation and pushing said device relative to said catheter hub such that said male-luer slip extends into said catheter hub and engages said internal wall of the catheter hub and such that said inner wall of said ring engages said external thread of the catheter hub;
   f) with said luer-slip engaging said internal wall of the catheter hub, and said inner wall of said ring engaging said external thread of the catheter hub, rotating said device relative to said catheter hub a plurality of times; and
   g) removing said device from catheter hub.

15. A method according to claim 14, wherein:
said second orientation is one hundred eighty degrees removed from said first orientation along a longitudinal axis of said device.

16. A method according to claim 14, wherein:
said grasping said device in a first orientation further comprises squeezing said first end of said device to cause said side wall to engage said external thread of said IV connector, and
said grasping said device in a second orientation further comprises squeezing said second end of said device to cause said inner wall of said ring to engage the external thread of the catheter hub.

17. A method according to claim 15, wherein:
said first end side wall defines at least one lateral slot, and said method further comprises,
prior to rotating said device relative to said IV connector a plurality of times, inspecting said device and said IV connector through said at least one lateral slot to confirm that said bottom surface of said blind hole engages said top surface of said IV connector.

18. A device for use in cleaning and disinfecting an intravenous (IV) connector having a female luer having an external thread and a top surface, and for use in disinfecting a vascular access catheter hub having an internal wall and an external thread, said device consisting of:
   a single piece of non-particulating compressible material having pores infused with a disinfectant agent,
   said single piece of material having a body with a first end and a second end,
   said first end defining a blind hole having a side wall and a bottom surface, said side wall adapted to be engageable with the external thread of the IV connector, and said blind hole having a depth chosen such that when said blind hole extends completely over the external thread of the IV connector, the top surface of the IV connector engages said bottom surface of the blind hole,
   said second end defining an annular recess with a ring having an inner wall about the annular recess at the second end of said body, and a male-luer slip extending from inside said recess to outside of said recess, said male-luer slip having a base inside said recess and a tip beyond said ring, said male-luer slip adapted to extend into the vascular access catheter hub and engage the internal wall of the catheter hub with an interference fit, and said inner wall of said ring adapted to be engageable the external thread of the catheter hub when the male-luer slip engages the internal wall of the catheter hub.

19. A device according to claim 18, wherein:
said blind hole has a depth of at least 0.25 inches, said luer-slip has a length of at least 0.43 inches from said base to said tip, said tip of said luer-slip has a diameter of approximately 0.16 inches, and said base of said luer slip has a diameter of approximately 0.18 inches, said luer-slip tapers from said base to said tip, and said inner wall is spaced approximately 0.07 inches from said luer-slip base.

20. A device according to claim 18, wherein:
said material comprises plastic.

* * * * *